United States Patent
Kikuchi et al.

(10) Patent No.: US 6,579,699 B1
(45) Date of Patent: Jun. 17, 2003

(54) METHOD FOR PRODUCING FERMENTATIVE PRODUCT AND STRESS-RESISTANT MICROORGANISM

(75) Inventors: Yoshimi Kikuchi, Kawasaki (JP); Osamu Kurahashi, Kawasaki (JP); Kenzo Yokozeki, Kawasaki (JP); Takashi Tanaka, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/371,010

(22) Filed: Aug. 10, 1999

(30) Foreign Application Priority Data

Aug. 11, 1998 (JP) .......................................... 10-227436

(51) Int. Cl.⁷ ......................... C12P 21/06; C12P 13/04; C12P 13/08; C12Q 1/68; C12N 1/20
(52) U.S. Cl. ......................... 435/69.1; 435/6; 435/106; 435/115; 435/169.1; 435/252.32; 435/252.33
(58) Field of Search .............................. 435/69.1, 169.1, 435/6, 91.1, 91.2, 106, 113–115, 252.32, 252.33, 843, 849, 471

(56) References Cited

U.S. PATENT DOCUMENTS 4,346,170 A * 8/1982 Sano et al.
5,188,949 A * 2/1993 Tsuchida et al.

FOREIGN PATENT DOCUMENTS

| EP | 0 488 424 | 6/1992 |
| EP | 0 774 512 | 5/1997 |
| EP | 0 864 654 | 9/1998 |
| JP | 9-173078 | 5/1997 |
| JP | 09173077 | * 7/1997 |
| WO | WO 96/26289 | 8/1996 |

OTHER PUBLICATIONS

Yan, Z., et al.: "In Vitro Stabilization and In Vivo Solubilization of Foreign Proteins by the Beta Subunit of a Chapernin from the Hyperthermophilic Archaeon Pyrococcus SP. Strain KOD1", Applied and Environmental Microbiology, U.S. , Washington, D.C., vol. 63, No. 2, Feb. 1, 1997, pp. 785–789, XP000673019.

Y. Izawa, et al: "Cloning and Analysis of the Heat Shock Protein Gene from a New Hyperthermophilic Archaeon, Pyrococcus SP. Strain KOD1", EMBL Nucleotide Sequence, XX, XX, Apr. 23, 1994, XP002029690.

* cited by examiner

Primary Examiner—Christopher R. Tate
Assistant Examiner—Michele C. Flood
(74) Attorney, Agent, or Firm—Oblon, Spivak, McClelland, Maier & Neustadt, P.C.

(57) ABSTRACT

A method for producing a fermentative product by utilizing a microorganism, the method comprising culturing the microorganism in a medium to produce and accumulate the fermentative product in the medium, and collecting the fermentative product, wherein the microorganism expresses a heat shock protein derived from a hyperthermophilic archaeon strain KOD-1 in a cell of the microorganism by introduction of a gene coding for the heat shock protein.

14 Claims, 1 Drawing Sheet

METHOD FOR PRODUCING FERMENTATIVE PRODUCT AND STRESS-RESISTANT MICROORGANISM

BACKGROUND OF THE INVENTION

The present invention relates to a method for producing a fermentative product. In particular, the present invention relates to a method for producing a useful substance such as an amino acid by fermentation utilizing a microorganism, and a microorganism to which resistance to stress that suppresses growth of the microorganism and/or production of a fermentative product by the microorganism is imparted.

When a cell is exposed to stress, such as high temperature, high osmotic pressure, metabolic inhibition, presence of heavy metal, and viral infection, synthesis of a family of proteins called "heat shock protein" (abbreviated as "HSP" hereinafter) is induced in a short period of time to cause defensive reactions against the stress. These HSPs show homology in a wide range from prokaryotic cells to eukaryotic cells, and they are roughly classified into several groups such as HSP60, HSP70, HSP90, TRiC, and other groups (Hendrick, J. P. and Hartl, F.-V., Annu. Rev. Biochem., 62, 349–384 (1993)).

The mechanism of the stress resistance imparted by the HSP is based on the function of the HSP to form higher-order structure of proteins (folding of proteins). Namely, the HSP can bind to a protein that has been denatured due to stress and become unable to form a correct higher order structure, and restore the normal function of the protein by refolding it into the correct higher order structure.

Because it has been elucidated that such function of the HSP in the formation of higher order structure of proteins serves as a molecular chaperon not only for denatured proteins but also for assembly, transmembrane transport and the like of proteins in normal cells, its importance has been recognized, and is attracting attentions (Ellis, R. J. et al., Science, 250, 954–959 (1990)). The term "chaperon" implies a supporter, and the name is given because the HSP exerts its function by binding to various proteins.

The expression of the HSP is induced when a cell is exposed to the stress as mentioned above. This induction is usually temporary. It is attenuated soon and reaches a new steady state. It has been revealed that this induction of the HSP is caused at transcription level (Cowing, D. C. et al., Proc. Natl. Acad. Sci. USA, 80, 2679–2683 (1985), Zhou, Y. N. et al., J. Bacteriol., 170, 3640–3649 (1988)). It has been known that a group of HSP genes commonly have a promoter structure called heat shock promoter, and that a factor specifically functioning for this heat shock promoter, $\sigma$–32 ($\sigma^{32}$) is present. It has also been known that $\sigma^{32}$ is encoded by rpoH gene, and it is a protein with a very short half life, about 1 minute, and closely relates to the temporary induction of the HSP (Straus, D. B. et al., Nature, 329, 348–351 (1987)). It has been shown that the expression control of $\sigma^{32}$ itself is attained at transcription level and translation level, but its major control is attained at translation level.

The induction of the HSP by heat shock is based on two mechanisms, i.e., increase in synthesized amount and stabilization of $\sigma^{32}$. Among these mechanisms, as for the increase of synthesis amount of $\sigma^{32}$, it has been revealed that the structure of $\sigma^{32}$ mRNA modified by heat enhances its translation (Yura, T. et al., Annu. Rev. Microbiol., 47, 321–350 (1993)). As for the stabilization of $\sigma^{32}$, involvement of an HSP (DnaK etc.) in the decomposition of $\sigma^{32}$ has been shown, and it is considered that feedback control by the HSP works (Tilly, K. et al., Cell, 34, 641–646 (1983), Liberek and K., Proc. Natl. Acad. Sci. USA, 89, 3516–3520 (1994)).

As for *Escherichia coli* (*E. coli*), a relationship between the HSP and growth of cells under the presence of stress have been known (Meury, J. et al., FEMS Microbiol. Lett., 113, 93–100 (1993)), and it has also been known that dnaK and groE affect on the-production of human growth hormones and the secretion of procollagenase, respectively (Hockney, R. C., Trends in Biotechnology, 12, 456 (1994)).

International Publication No. WO96/26289 describes that resistance to stress that inhibits microorganism growth and/or fermentative product production can be imparted to a microorganism by introducing at least one of a gene coding for an HSP and a gene coding for a $\sigma$ factor which specifically functions for an HSP, into the microorganism to enhance an expression amount of an HSP.

SUMMARY OF THE INVENTION

The object of the present invention is, in the production of a useful substance such as an amino acid by fermentation, to further improve productivity and yield of the fermentative product by reducing the influence of stress that inhibits microorganism growth and/or fermentative product production.

The present inventors conducted studies in order to achieve the aforementioned object. As a result, they sound that the productivity and the growth could be further improved under a high stress condition by introducing a gene coding for HSP derived from a hyperthermophilic archaeon strain KOD-1 into a microorganism to express the HSP, and accomplished the present invention.

Thus, the present invention provides a method for producing a fermentative product by utilizing a microorganism, the method comprising culturing the microorganism in a medium to produce and accumulate the fermentative product in the medium, and collecting the fermentative product, wherein the microorganism expresses an HSP derived from the hyperthermophilic archaeon strain KOD-1 in a cell of the microorganism by introduction of a gene coding for the HSP.

The present invention also provides a microorganism producing a fermentative product, which expresses an HSP derived from the hyperthermophilic archaeon strain KOD-1 in a cell of the microorganism by introduction of a gene coding for the HSP.

In the aforementioned method and microorganism of the present invention, the fermentative product may be, for example, an amino acid such as L-threonine, L-lysine, L-glutamic acid, L-leucine, L-isoleucine, L-valine, and L-phenylalanine, a nucleic acid or a nucleoside such as guanylic acid, inosine, and inosinic acid, a vitamin, an antibiotic or the like, and an amino acid is preferred.

As the microorganism to which the present invention can be applied, bacteria belonging to the genus Escherichia and coryneform bacteria can be mentioned.

According to the present invention, in the production of useful substances such as amino acids by fermentation, the influence of stress can be further decreased, and productivity and yield can be further improved.

DETAILED DESCRIPTION OF THE INVENTION

Figure 1:
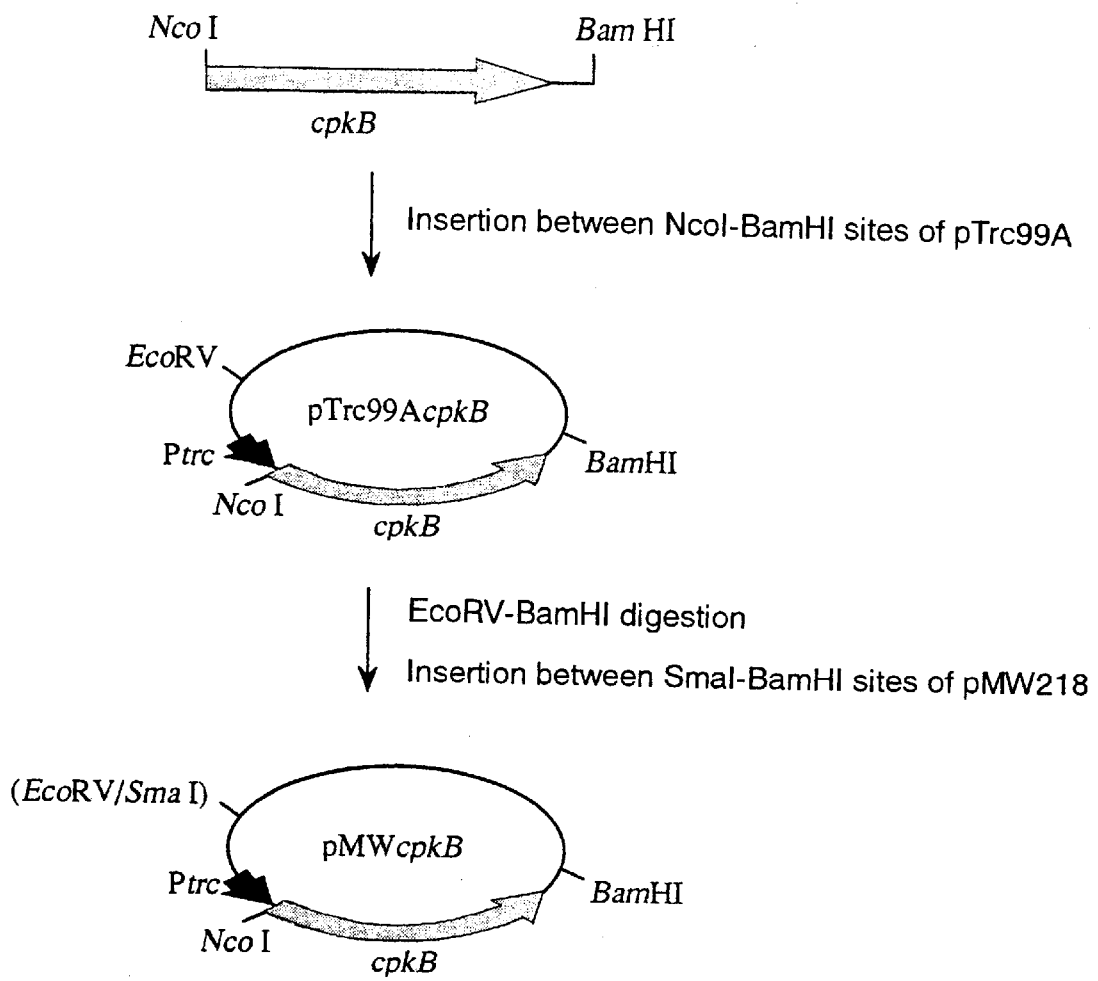
FIG. 1 is an explanatory drawing representing the construction of plasmid pMWcpkB.

The present invention will be explained in detail hereinafter.

The fermentative product to which the present invention can be applied is not particularly limited so long as it can be produced by fermentation utilizing a microorganism. Examples thereof include those produced by microorganisms, for example, various L-amino acids such as L-threonine, L-lysine, L-glutamic acid, L-leucine, L-isoleucine, L-valine, and L-phenylalanine, nucleic acids and nucleosides such as guanylic acid, inosine, and inosinic acid, vitamins, antibiotics and the like. Moreover, the present invention may be applied even to a substance that is not produced by utilizing microorganisms at present, once it becomes to be produced by utilizing microorganisms according to genetic recombination technique or the like. Among the aforementioned substances, the method of the present invention can be suitably applied to those secreted and accumulated in a medium and thereby increasing osmotic pressure of medium, especially, like amino acids.

The microorganism which is used to express the HSP derived from the hyperthermophilic archaeon strain KOD-1 in its cell by introduction of a gene coding for the HSP is not particularly limited so long as it produces a fermentative product by fermentation. Examples thereof include those conventionally used for the production by fermentation, for example, bacteria belonging to the genus Escherichia, coryneform bacteria, bacteria belonging to the genus Bacillus, bacteria belonging to the genus Serratia and the like. The microorganism is preferably a microorganism of which DNA fragment containing a replication origin for plasmid is obtained, and in which the aforementioned HSP gene can function, and copy number of the gene can be increased. The aforementioned coryneform bacteria refer to those of the microorganism class defined in Bargey's Manual of Determinative Bacteriology, 8th Edition, p. 599 (1974), and are aerobic, gram positive and non-acid-fast bacilli not having spore-forming ability. They include bacteria belonging to the genus Corynebacterium, those of bacteria belonging to the genus Brevibacterium formerly categorized into the genus Brevibacterium but currently classified as bacteria belonging to the genus Corynebacterium, and bacteria belonging to the genus Brevibacterium close to bacteria belonging to the genus Corynebacterium.

Specifically, such a microorganism as mentioned above may be *Escherichia coli* VKPM B-3996 (RIA1867, see U.S. Pat. No. 5,175,107), *Corynebacterium acetoacidophilum* AJ12318 (FERM BP-1172, see U.S. Pat. No. 5,188,949) or the like for L-threonine; *Escherichia coli* AJ11442 (NRRL B-12185 and FERM BP-1543, see U.S. Pat. No. 4,346,170), *Escherichia coli* W3110 (tyrA) (this strain can be obtained by removing plasmid pHATerm from *Escherichia coli* W3110 (tyrA)/pHATerm (FERM BP-3653), see International Publication No. WO95/16042), *Brevibacterium lactofermentum* AJ12435 (FERM BP-2294, see U.S. Pat. No. 5,304,476), *Brevibacterium lactofermentum* AJ3990 (ATCC 31269, see U.S. Pat. No. 15 4,066,501) or the like for L-lysine; *Escherichia coli* AJ12624 (FERM BP-3853, see French Patent Publication No. 2,680,178), *Brevibacterium lactofermentum* AJ12821 (FERM BP-4172, Japanese Patent Application Laid-Open No. 5-26811 (1993), French Patent Publication No. 2,701,489), *Brevibacterium lactofermentum* AJ12475 (FERM BP-2922, see U.S. Pat. No. 5,272,067), *Brevibacterium lactofermentum* AJ13029 (FERM BP-5189, see International Publication No. WO96/06180) or the like for L-glutamic acid; *Escherichia coli* AJ11478 (FERM P-5274, see Japanese Patent Publication No. 62-34397 (1987)), *Brevibacterium lactofermentum* AJ3718 (FERM P-2516, see U.S. Pat. No. 3,970,519) or the like for L-leucine; *Escherichia coli* KX141 (VKPM B-4781, see European Patent Publication No. 519,113), *Brevibacterium flavum* AJ12149 (FERM BP-759, see U.S. Pat. No. 4,656, 135) or the like for L-isoleucine; *Escherichia coli* VL1970 (VKPM B-4411, see European Patent Publication No. 519, 113), *Brevibacterium lactofermentum* AJ12341 (FERM BP-1763, see U.S. Pat. No. 5,188,948) or the like for L-valine; *Escherichia coli* AJ12604 (FERM BP-3579, Japanese Patent Application Laid-Open No. 5-236947 (1993), European Patent Publication No. 488,424), *Brevibacterium lactofermentum* AJ12637 (FERM BP-4160, see French Patent Publication No. 2,686,898) or the like for L-phenylalanine.

The microorganism of the present invention is such a microorganism as mentioned above in which the HSP derived from the hyperthermophilic archaeon strain KOD-1 is expressed in its cell by introducing a gene coding for the HSP. By this expression of the HSP, resistance to stress that inhibits growth of the microorganism and/or production of the fermentative product by the microorganism is given to the microorganism.

The gene coding for the HSP of the hyperthermophilic archaeon strain KOD-1 is preferably introduced in such a manner that the expression amount of the HSP should be increased. Specifically, the copy number of an HSP gene in a cell can be increased by utilizing a vector autonomously replicable in a microbial cell, especially a multi-copy type plasmid, as a vector for introduction of the HSP gene into the microbial cell. Further, the expression of HSP can also be efficiently enhanced by increasing the expression amount per HSP gene through use of a promoter having high expression efficiency.

The gene coding for the HSP derived from the hyperthermophilic archaeon strain KOD-1 can be obtained by the method described in Japanese Patent Application Laid-Open No. 9-173078 (1997). Specifically, it can be obtained by, for example, the method by performing PCR utilizing chromosome DNA prepared from the hyperthermophilic archaeon strain KOD-1 (Appl. Environ. Microbiol., 60 (12), 4559–4566 (1994)) as a template, and oligonucleotides prepared based on the nucleotide sequence of the gene coding for the HSP derived from the hyperthermophilic archaeon strain KOD-1 disclosed in Japanese Patent Application Laid-Open No. 9-173078 (1997) and the like as primers. Examples of the oligonucleotides used for the primers are oligonucleotides having the nucleotide sequences shown as SEQ ID NOS: 8 and 9 in Japanese Patent Application Laid-Open No. 9-173078 (1997).

The gene coding for the HSP of the hyperthermophilic archaeon strain KOD-1 can also be obtained as a plasmid incorporating a DNA fragment containing this gene. As such a plasmid, plasmid pTrc99AcpkB can be mentioned, and *Escherichia coli* JM109 harboring this plasmid pTrc99AcpkB was designated as *Escherichia coli* AJ13478, and it was deposited at the National Institute of Bioscience and Human-Technology, Agency of Industrial Science and Technology, Ministry of International Trade and Industry (postal code 305–0046, 1–3, Higashi 1-chome, Tsukuba-shi, Ibaraki-ken, Japan) on Jul. 8, 1998, and received an accession number of FERM P-16887. This deposition was thereafter transferred to an international deposition under the Budapest Treaty on Jun. 14, 1999, and received an accession number of FERM BP-6758.

In order to introduce the gene obtained as described above into a bacterium belonging to the genus Escherichia, for example, a DNA fragment containing the aforementioned gene can be ligated to a vector DNA which can autonomously replicate in a cell of the bacterium, and the bacterium can be transformed with the obtained recombinant vector. In order to introduce the above gene into a microorganism other than bacteria belonging to the genus Escherichia, for example, a DNA fragment containing the aforementioned gene can be ligated to a vector DNA which can autonomously replicate in the microorganism, and the microorganism can be transformed with the obtained recombinant vector.

As the vector DNA that can be used in the present invention, a plasmid vector DNA is preferred. When the microorganism into which the gene is introduced is a bacterium belonging to the genus Escherichia, pUC19, pUC18, pBR322, pHSG299, pHSG399, RSF1010 and the like can be used, for example. Vectors of phage DNA can also be utilized. In order to obtain efficient expression of the HSP, a promoter functioning in microorganisms, such as lac, trp, and PL, may be used instead of the promoter of the HSP gene's own. In order to introduce the HSP gene into a microorganism, a DNA containing the gene can be incorporated into a chromosome of the aforementioned microorganism by a method utilizing a transposon (Berg, D. E. and Berg, C. M., Bio/Technol., 1, 417 (1983)), Mu phage (Japanese Patent Application Laid-Open No. 2-109985 (1990)), or homologous recombination (Experiments in Molecular Genetics, Cold Spring Harbor Lab. (1972)). Moreover, when the microorganism to which the gene is introduced is a coryneform bacterium, a plasmid vector which can autonomously replicate in coryneform bacteria, for example, pMA330 (see Japanese Patent Publication No. 1-11280 (1989)), pHM1519 (see Japanese Patent Application Laid-Open No. 58-77895 (1983)) and the like can be used.

The transformation can be attained according to conventional production of transformants of microorganisms. For example, bacteria belonging to the genus Escherichia can be transformed by the method of D. A. Morrison (Methods in Enzymology, 68, 326 (1979)) or a method in which recipient cells are treated with calcium chloride to increase permeability for DNA (Mandel, M. and Higa, A., J. Mol. Biol., 53, 159 (1970)). The transformation of coryneform bacteria can be attained by the aforementioned method of Mandel et al., or a method utilizing introduction of DNA into a cell at a growth phase (so-called competent cell) so that the cell can incorporate the DNA as reported for Bacillus subtilis (Duncan, C. H., Wilson, G. A., and Young, F. E., Gene, 1, 153 (1977)). It is also possible to prepare a protoplast or spheroplast of a DNA-recipient strain, which readily incorporates DNA, and introduce DNA into it as known for Bacillus subtilis, Actinomycetes and yeast (changs, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B., and Fink, G. R., Proc. Natl. Acad. Sci. USA, 75, 1929 (1978)). Further, it is also possible to introduce a recombinant DNA into bacteria belonging to the genus Brevibacterium or Corynebacterium by utilizing the electric pulse technique (Sugimoto et al., Japanese Patent Application Laid-Open No. 2-207791 (1990)).

When an ordinary microorganism is exposed to stress such as elevation of culturing temperature, high osmotic pressure caused by a fermentative product, a high concentration medium ingredient or the like, or metabolic abnormality associated with the production of a target fermentative product, its growth may be inhibited or the productivity of the fermentative product may be reduced. However, by expressing the HSP derived from the hyperthermophilic archaeon strain KOD-1, excellent resistance to the stress can be imparted to the microorganism. As a result, the productivity of the fermentative product can further be improved under the circumstance where the microorganism is exposed to such stress as mentioned above. Therefore, the expression of the above HSP in a microorganism to which the gene coding for the HSP derived from the hyperthermophilic archaeon strain KOD-1 strain has been introduced to express the HSP in its cell may also be confirmed by evaluation of the above stress resistance, in addition to direct detection of the HSP.

The resistance to stress may not be complete resistance, and also implies a characteristic to decrease the influence from the stress. Further, depending on the kind of genes to be introduced and the kind of host microorganisms, both of the inhibition of growth and the reduction of the yield of the fermentative product are not necessarily improved, and only the yield of the fermentative product may be improved while the growth may be inhibited. The stress to which resistance can be given by the method of the present invention includes temperature (e.g., elevated temperature), osmotic pressure of medium (e.g., high osmotic pressure), high concentration of an amino acid in a medium and the like, which are undesirable for the microorganism growth.

The medium for the production by fermentation used for the present invention may be a conventionally-used well-known medium. Namely, it may be an ordinary medium containing a carbon source, a nitrogen source, inorganic ions, and other organic components as required. Any special medium is not required for the practice of the present invention.

As the carbon source, a saccharide such as glucose, lactose, galactose, fructose and starch hydrolysates, an alcohol such as glycerol and sorbitol, an organic acid such as fumaric acid, citric acid and succinic acid and the like may be used.

As the nitrogen source, an inorganic ammonium salt such as ammonium sulfate, ammonium chloride, and ammonium phosphate, an organic nitrogen source such as soy bean hydrolysates, ammonia gas, aqueous ammonia and the like may be used.

As the trace organic nutrient, it is desirable to add suitable amounts of required substances such as vitamin $B_1$, L-homoserine, and L-tyrosine, or yeast extract and the like. Other than these, a trace amount of potassium phosphate, magnesium sulfate, iron ions, manganese ions and the like are added as required.

The culture may be performed under conditions selected from the conventionally-used well-known conditions depending on the kind of microorganisms to be used. For example, the culture may be performed under an aerobic condition for 16 to 120 hours while controlling fermentation temperature from 25 to 45° C., and pH from 5 to 8. In order to adjust pH, organic or inorganic acidic or alkaline substances, and ammonia gas and the like may be used.

Any special means is not required in the present invention for the collection of fermentative product from the culture medium after the culture is completed. Namely, the metabolic product produced according to the present invention can be collected by a well-known conventional means, for example, ion exchange chromatography, precipitation, any combination of these or other techniques or the like.

EXAMPLES

The present invention will be explained more specifically with reference to the following examples.

Example 1

L-Lysine production by L-lysine-producing *Escherichia coli* into which gene coding for HSP derived from the hyperthermophilic archaeon strain KOD-1 (cpkB gene) is introduced.

*Escherichia coli* W3110 (tyrA) was used as a host for L-lysine production. While the strain W3110 (tyrA) is described in European Patent Publication No. 488424 in detail, the preparation method therefor will be outlined below. *E. Coli* W3110 was obtained from the National Institute of Genetics (Mishima-shi, Shizuoka, Japan). This strain was inoculated on a LB plate containing streptomycin, and a streptomycin-resistant strain was obtained by selecting a strain that formed a colony. The cells of the selected streptomycin-resistant strain and *E. coli* K-12 ME8424 were mixed, and cultured as standing culture for 15 minutes at 37° C. in a complete medium (L-Broth: 1% Bacto trypton, 0.5% yeast extract, 0.5% NaCl) to induce cell conjugation. The *E. coli* K-12 ME8424 has genetic characters of (HfrPO45, thi, relA1, tyrA::Tn10, ung-1, nadB), and can be obtained from the National Institute of Genetics. Then, the culture was inoculated to a complete medium (L-Broth: 1% Bacto trypton, 0.5% yeast extract, 0.5% NaCl, 1.5% agar) containing streptomycin, tetracycline, and L-tyrosine, and a strain which formed a colony was selected. This strain was designated as *E. coli* W3110 (tyrA).

Many strains produced by introducing a plasmid into this strain are disclosed in European Patent Publication No. 488424. For example, a strain produced by introducing plasmid pHATerm into the strain was designated as *Escherichia coli* W3110 (tyrA)/pHATerm, and it was deposited at the National Institute of Bioscience and Human-Technology, Agency of Industrial Science and Technology, Ministry of International Trade and Industry (postal code 305-0046, 1–3, Higashi 1-chome, Tsukuba-shi, Ibaraki-ken, Japan) on Nov. 16, 1991 as an international deposition under the Budapest Treaty, and received an accession number of FERM BP-3653. The *Escherichia coli* W3110 (tyrA) can be obtained by removing the plasmid pHATerm from the above strain by using an ordinary method.

The plasmid pCABD2 containing lysine biosynthesis genes, which is disclosed in International Publication No. WO95/16042, was introduced into the above *Escherichia coli* W3110 (tyrA). The transformant into which the plasmid was introduced was selected on an L plate medium (containing 10 g of polypeptone, 5 g of yeast extract, 5 g of NaCl, and 15 g of agar in 1 L of pure water, pH 7.2) containing 50 µg/ml of streptomycin.

On the other hand, a plasmid for introducing cpkB was constructed as follows. A PCR fragment containing the cpkB gene was obtained according to the method described in Example 5 of Japanese Patent Application Laid-Open No. 9-173078 (1997)), and digested with NcoI and BamHI. The excised fragment was cloned between the NcoI and BamHI sites of a vector plasmid pTrc99A (produced by Pharmacia) to obtain a plasmid pTrc99AcpkB. *Escherichia coli* JM109 harboring the plasmid pTrc99AcpkB was designated as *Escherichia coli* AJ13478, and it was deposited at the National Institute of Bioscience and Human-Technology, Agency of Industrial Science and Technology, Ministry of International Trade and Industry (postal code 305-0046, 1–3, Higashi 1-chome, Tsukuba-shi, Ibaraki-ken, Japan) on Jul. 8, 1998, and received an accession number of FERM P-16887. This deposition was thereafter transferred to an international deposition under the Budapest Treaty on Jun. 14, 1999, and received an accession number of FERM BP-6758. Further, a cpkB gene fragment containing added trc promoter, which was excised by digestion of the plasmid pTrc99AcpkB with EcoRV and BamHI, was cloned between the SmaI and BamHI sites of pMW218 (produced by Wako Pure Chemical Industries) to obtain a plasmid pMWcpkB. The outline of the construction of this plasmid is shown in FIG. 1. This pMWcpkB was introduced into a cell of *Escherichia coli* W3110 (tyrA)/pCABD2 by the aforementioned method. A transformant cell into which the plasmid was introduced was selected on L plate medium containing 50 µg/ml of streptomycin and 50 µg/ml of kanamycin.

Further, a plasmid for introducing rpoH gene was constructed as follows. The rpoH gene was amplified by the PCR technique described in Example 1 <1> of International Publication No. WO96/26289, and the obtained amplification product was blunt-ended at the both ends by using a commercially available kit for blunt-ending DNA termini (Blunting kit, produced by Takara Shuzo), and cloned into the HincII site of a vector plasmid pMW119 (produced by Wako Pure Chemical Industries) to obtain a plasmid pMWrpoH. This plasmid was introduced into the *Escherichia coli* W3110 (tyrA)/pCABD2 by the method mentioned above. A transformant cell into which the plasmid was introduced was selected on L plate medium containing 50 µg/ml of streptomycin and 50 µg/ml of ampicillin.

L-Lysine productivity of the *Escherichia coli* W3110 (tyrA)/pCABD2, *Escherichia coli* W3110 (tyrA)/pCABD2+pMWrpoH, and *Escherichia coli* W3110 (tyrA)/pCABD2+pMWcpkB obtained as described above was evaluated.

The evaluation of L-lysine productivity of the obtained transformants was performed as follows. The cells were refreshed by culturing them on an L plate medium, and each refreshed transformant was cultured at 37° C. for 30 hours in a medium containing 40 g of glucose, 1 g of $KH_2PO_4$, 0.01 g of $MnSO_4.7H_2O$, 0.01 g of $FeSO_4.7H_2O$, 2 g of yeast extract, 0.1 g of L-tyrosine, 1 g of $MgSO_4.7H_2O$, and 25 g of $CaCO_3$ in 1 L of pure water (pH was adjusted to 7.0 with KOH). The cells were also cultured in the same manner except that 40 g/L of L-lysine hydrochloride was added at the time of starting the culture. Quantitative assay of L-lysine was performed by using Biotech Analyzer AS210 produced by Asahi Chemical Industry Co., Ltd. The produced amount of L-lysine (the amount obtained by subtracting the initially added amount of L-lysine from the amount of L-lysine in the medium after the culture) was represented as a yield of L-lysine hydrochloride based on the saccharide in the medium (% by weight). The results are shown in Table 1.

TABLE 1

| Strain | Yield of L-lysine hydrochloride based on saccharide(%) Initially added L-lysine hydrochloride (g/L) | |
| --- | --- | --- |
| | 0 | 40 |
| W3110 (tyrA)/pCABD2 | 30.0 | 27.4 |
| W3110 (tyrA)/pCABD2 + pMWrpoH | 30.2 | 28.8 |
| W3110 (tyrA)/pCABD2 + pMWcpkB | 30.4 | 29.3 |

From these results, it is clear that *Escherichia coli* into which the cpkB gene is introduced exhibits improved L-lysine productivity even in the presence of L-lysine at a high concentration compared with the strain into which the cpkB gene is not introduced and the strain into which the rpoH gene is introduced.

Further, L-lysine productivity was similarly evaluated under the condition that 22 g/L of NaCl was added at the time of starting the culture. The results are shown in Table 2.

TABLE 2

| Strain | Yield of L-lysine hydrochloride based on saccharide(%) Initially added NaCl (g/L) | |
|---|---|---|
| | 0 | 22 |
| W3110 (tyrA)/pCABD2 | 30.0 | 24.3 |
| W3110 (tyrA)/pCABD2 + pMWrpoH | 30.2 | 25.0 |
| W3110 (tyrA)/pCABD2 + pMWcpkB | 30.4 | 25.5 |

From these results, it is clear that *Escherichia coli* into which the cpkB gene is introduced exhibits improved L-lysine productivity even in the presence of NaCl at a high concentration compared with the strain into which the CpkB gene is not introduced and the strain into which the rpoH gene is introduced. Therefore, it has been found that it has excellent resistance to a high osmotic pressure.

Then, the influence of culture temperature for L-lysine production was investigated. L-Lysine productivity was evaluated in the same manner as described above except that the culture was carried out at 37° C. as a standard condition and at 42° C. The results are shown in Table 3.

TABLE 3

| Strain | Yield of L-lysine hydrochloride based on saccharide(%) Culture temperature (° C.) | |
|---|---|---|
| | 37 | 42 |
| W3110 (tyrA)/pCABD2 | 30.0 | 26.3 |
| W3110 (tyrA)/pCABD2 + pMWrpoH | 30.2 | 27.7 |
| W3110 (tyrA)/pCABD2 + pMWcpkB | 30.4 | 27.9 |

From these results, it is clear that *Escherichia coli* into which the cpkb gene is introduced exhibits improved L-lysine productivity even in the culture at a high temperature compared with the strain into which the cpkB gene is not introduced and the strain into which the rpoH gene is introduced.

What is claimed is:

1. A method for producing an amino acid by utilizing a microorganism, the method comprising culturing the microorganism in a medium to extracellularly produce and accumulate the amino acid in the medium, and collecting the amino acid, wherein a gene coding for a heat shock protein derived from hyperthermophilic archaeon strain KOD-1 is introduced into the microorganism so that the microorganism expresses the heat shock protein derived from the hyperthermophillic archaeon strain KOD-1 in a cell of the microorganism.

2. The method according to claim 1 wherein the microorganism is a bacterium belonging to the genus Escherichia or a coryneform bacterium.

3. The method of claim 1, wherein the gene coding for a hyperthermophillic archaeon strain KOD-1 heat shock protein is cpkb.

4. The method of claim 1, wherein the gene coding for a hyperthermophillic archaeon strain KOD-1 heat shock protein is on a plasmid.

5. The method of claim 4, wherein the plasmid is pTRc99AcpkB.

6. The method of claim 1, wherein the gene coding for a hyperthermophillic archaeon strain KOD-1 heat shock protein is operably linked to a promoter selected from the group consisting of lac promoter, trp promoter, and PL promoter.

7. The method of claim 1, wherein the amino acid is L-lysine.

8. A method of producing an amino acid, comprising introducing a gene coding for a hyperthermophillic archaeon strain KOD-1 heat shock protein into a microorganism, culturing the microorganism in a medium to extracellularly produce and accumulate the amino acid, and collecting the amino acid.

9. The method of claim 8, wherein the microorganism is a Escherichia or a coryneform bacterium.

10. The method of claim 8, wherein the gene coding for a hyperthermophillic archaeon strain KOD-1 heat shock protein is cpkB.

11. The method of claim 8, wherein the gene coding for a hyperthermophillic archaeon strain KOD-1 heat shock protein is on a plasmid.

12. The method of claim 11, wherein the plasmid is pTRc99AcpkB.

13. The method of claim 8, wherein the gene coding for a hyperthermophillic archaeon strain KOD-1 heat shock protein is operably linked to a promoter selected from the group consisting of lac promoter, trp promoter, and PL promoter.

14. The method of claim 8, wherein the amino acid is L-lysine.

* * * * *